United States Patent [19]

Liang et al.

[11] Patent Number: 5,606,975
[45] Date of Patent: Mar. 4, 1997

[54] FORWARD VIEWING ULTRASONIC IMAGING CATHETER

[75] Inventors: David H. Liang; Bob S. Hu, both of Menlo Park, Calif.

[73] Assignee: The Board of Trustees of the Leland Stanford Junior University, Stanford, Calif.

[21] Appl. No.: 309,540

[22] Filed: Sep. 19, 1994

[51] Int. Cl.$^6$ ........................................ A61B 8/12
[52] U.S. Cl. .......................... 128/662.06; 128/660.1
[58] Field of Search ................ 128/660.03, 662.06, 128/660.1; 606/159; 600/103, 109, 160

[56] References Cited

U.S. PATENT DOCUMENTS

| | | | |
|---|---|---|---|
| 4,479,388 | 10/1984 | Matzuk | 73/634 |
| 4,489,728 | 12/1984 | Matsuo et al. | 128/660 |
| 4,587,972 | 5/1986 | Morantte, Jr. | 128/660 |
| 4,794,931 | 1/1989 | Yock | 128/660.03 |
| 4,841,977 | 6/1989 | Griffith et al. | 128/660.03 |
| 4,917,097 | 4/1990 | Proudian et al. | 128/662.06 |
| 5,000,185 | 3/1991 | Yock | 128/662.03 |
| 5,156,144 | 10/1992 | Iwasaki et al. | 128/24 EL |
| 5,170,793 | 12/1992 | Takano et al. | 128/662.06 |
| 5,240,003 | 8/1993 | Lancee et al. | 128/662.06 |
| 5,243,988 | 9/1993 | Sieben et al. | 128/662.06 |
| 5,271,402 | 12/1993 | Yeung et al. | 128/660.1 |
| 5,284,148 | 2/1994 | Dias et al. | 128/662.06 |
| 5,313,949 | 5/1994 | Yock | 128/662.06 |
| 5,313,950 | 5/1994 | Ishikawa et al. | 128/662.06 |
| 5,353,798 | 10/1994 | Sieben | 128/662.06 |
| 5,368,035 | 11/1994 | Hamm et al. | 128/662.06 |
| 5,368,037 | 11/1994 | Eberle et al. | 128/662.06 |
| 5,373,845 | 12/1994 | Gardineer et al. | 128/660.09 |
| 5,373,849 | 12/1994 | Maroney et al. | 128/662.06 |
| 5,375,602 | 12/1994 | Lancee et al. | 128/662.06 |
| 5,377,685 | 1/1995 | Kazi et al. | 128/662.06 |
| 5,379,772 | 1/1995 | Imran | 128/662.06 |
| 5,438,997 | 8/1995 | Sieben et al. | 128/662.06 |
| 5,445,155 | 8/1995 | Sieben | 128/660.07 |

FOREIGN PATENT DOCUMENTS

| | | | |
|---|---|---|---|
| 4-9149A | 4/1990 | Japan . | |
| 4009149 | 1/1992 | Japan | 128/662.06 |
| 2263974 | 8/1993 | United Kingdom | 128/662.06 |
| WO92/16140 | 1/1992 | WIPO . | |

OTHER PUBLICATIONS

Winston, T. "Catheter for Laser Treatment . . . " Int. Appln WO92/16140 published 01 Oct. 1992.

Detre et al., Percutaneous Transluminal Coronary Angioplasty in 1985–1986: The National Heart, Lung and Blood Institute Registry, New England Jor. of Med., 318:265–270, 1988.

Evans et al., Arterial Imaging with a New Forward–Viewing Intravascular Ultrasound Catheter, I: Initial Studies, Circulation, 89(2):712–717, Feb. 1994.

Ng et al., Arterial Imaging with a New Forward–Viewing Intravascular Ultrasound Catheter, II: Initial Studies, Circulation, 89(2):718–723, Feb. 1994.

Simpson et al., Factors Associated with Restenosis Following Directional Coronary Atherectomy of Primary Lesions in Native Coronary Arteries, p. I–531, Oct. 1992.

Topol et al., Analysis of Coronary Angioplasty in the United States with an Insurance–Claims Database, Circulation, 87:1489–1497, 1993.

*Primary Examiner*—Francis Jaworski
*Attorney, Agent, or Firm*—Townsend and Townsend and Crew; Henry K. Woodward

[57] ABSTRACT

A simple forward viewing ultrasound catheter includes one or more transducers and an ultrasound mirror supported by a bearing in a sealed end of a catheter with a drive cable imparting relative motion to the transducer and mirror. The mirror directs ultrasound waves forward of the catheter. An optical fiber can be provided to direct a laser beam for ablation of atheroma while under guidance of simultaneous intravascular ultrasound.

24 Claims, 14 Drawing Sheets

FORWARD VIEWING ULTRASONIC IMAGING CATHETER

BACKGROUND OF THE INVENTION

This invention relates generally to blood vessel imaging, and more particularly the invention relates to forward viewing intravascular ultrasound imaging.

Coronary artery disease is the number one cause of mortality in the United States and peripheral vascular disease remains a major cause of morbidity. Percutaneous interventions have rapidly developed to address the blockages in the blood vessels which result in angina, heart attacks and limb ischemia. In 1990 greater than 300,000 coronary angioplasties were performed in the United States. The methods for addressing these blockages include balloon angioplasty as well as many newer technologies such as excimer lasers, directional coronary atherectomy and high speed rotational burrs. The traditional and still primary method for guiding these interventions in angiography. Angiography is limited to defining the size and course of the lumen of the blood vessel and therefore gives little information about the actual structure and geometry of the blockage and the blood vessel wall. Because of this limited image guidance and primitive intervention devices, the incidence of acute complications remains significant, with a 3 to 5% rate of myocardial infarction and 1 to 2% death rate. More importantly, the lack of adequate visualization results in inadequate removal of the blockage and may contribute to the high rate of recurrence.

Newer methods of visualization of the blood vessel have become available in the past few years. Angioscopy allows visualization of the optical characteristics of the surface of the blockage but gives no information about the underlying shape and structure of the blockage. Furthermore, angioscopy requires large amounts of flushing to keep the field of view clear. Thus, angioscopy remains a poor method for guiding intervention.

Intravascular ultrasound has many of the properties of an ideal system for evaluating blockages and other lesions in blood vessels. The creation of images based on echo delay times results in visualization of the internal structure of the blockages and other lesions in blood vessels. The creation of images based on echo delay times results in visualization of the internal structure of the blockage and of the arterial wall. Furthermore, since blood is relatively echolucent, no flushing is required to maintain an image, therefore continuous imaging during intervention is feasible.

The current generation of intravascular ultrasound devices are all essentially side looking devices. As such, the device must be passed through the blockage in order for it to visualize the blockage. Since the smallest of the current generation of devices is 2.9 Fr (1 mm in diameter), the ultrasound catheter usually cannot be advanced through a significant blockage without disturbing it. In the case of complete occlusions, the ultrasound catheter cannot be used at all.

A forward looking ultrasound device, that is a device which is not restricted to side looking, would permit the evaluation of blockages without disturbing them and potentially serve as a useful tool for guiding recanalization of complete occlusions. The need for such a device has been discussed for many years. Some degree of forward imaging has been proposed in the past by angling the mirror used to redirect the ultrasound beam so that a conical section is obtained, rather than the radial slice that results from a typical side looking transducer. The conical sections obtained by this approach are not well suited for assessing the degree of atherosclerosis or for assessing the size of the lumen.

An implementation of a true forward viewing sector scanner was recently described which uses a complex mechanical linkage to achieve the forward scanning. The complexity of this approach, however, has resulted in a bulky device which measures 4 mm (14 Fr) in diameter. A device of this dimension, although possibly suitable for use in the peripheral vasculature, could not be used in the coronary circulation.

In order to achieve the goal of a catheter suitable for evaluating coronary arteries as well as peripheral vessels, the device dimensions should be such that it will fit comfortably in a vessel 3 mm in diameter. Therefore, the catheter diameter should be less than 2 mm and ideally under 1.5 mm. Furthermore, to provide useful images, the device will ideally provide 1 cm of penetration to permit complete visualization of most blockages and provide a 50 degree scan sector so that the scan will subtend a typical 3–5 mm diameter vessel.

The present invention is directed to a mechanical sector scanner for achieving these goals.

SUMMARY OF THE INVENTION

In accordance with one embodiment of the invention, an intravascular ultrasound imaging catheter includes an ultrasound transducer and an ultrasound reflective mirror supported by bearing means in a distal end of the catheter. A drive means such as a cable imparts relative motion to the transducer and mirror whereby ultrasonic waves are transmitted forward of the sealed end to provide blood vessel imaging. An optical fiber can be provided to direct a laser beam for ablation of atheroma while under the guidance of simultaneous intravascular ultrasound.

In specific embodiments, the transducer can be held stationary while the mirror is rotated, the mirror can be held stationary while the transducer is rotated, or relative motion can be imparted whereby both the transducer and the mirror are rotated by means of planetary gears in the bearing means. Further, a plurality of stationary transducers can be positioned around the mirror and selectively energized as the mirror is rotated.

In accordance with another embodiment of the invention, the ultrasound transducer is rotatably or pivotally mounted in a housing for transmitting a scanned ultrasound beam in response to a suitable microactuator driving mechanism such as an electrostatic or electromagnetic responsive element.

The invention and objects and features thereof will be more readily apparent from the following description and appended claims when taken with the drawings.

DETAILED DESCRIPTION OF THE ILLUSTRATIVE EMBODIMENTS

Figure 1A:
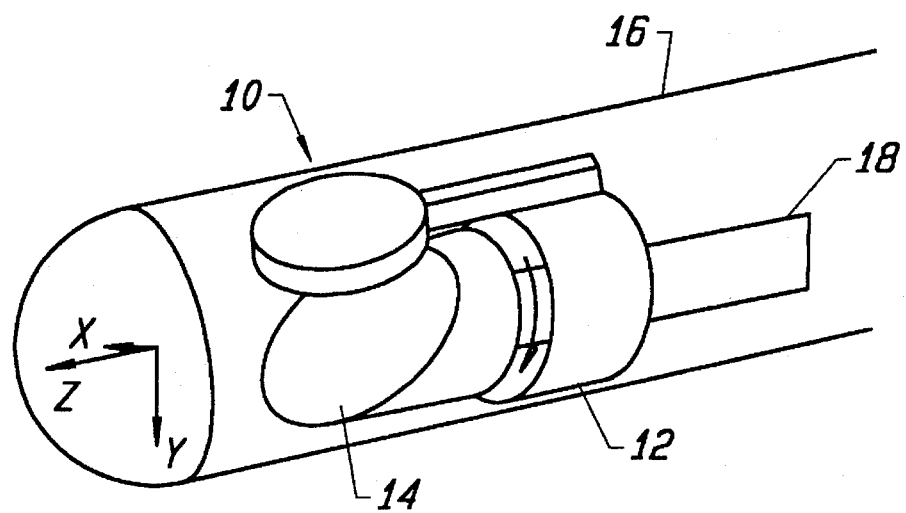
FIGS. 1A, 1B illustrate in perspective and in section view an intravascular ultrasound imaging catheter in accordance with one embodiment of the invention.
Figure 1B:
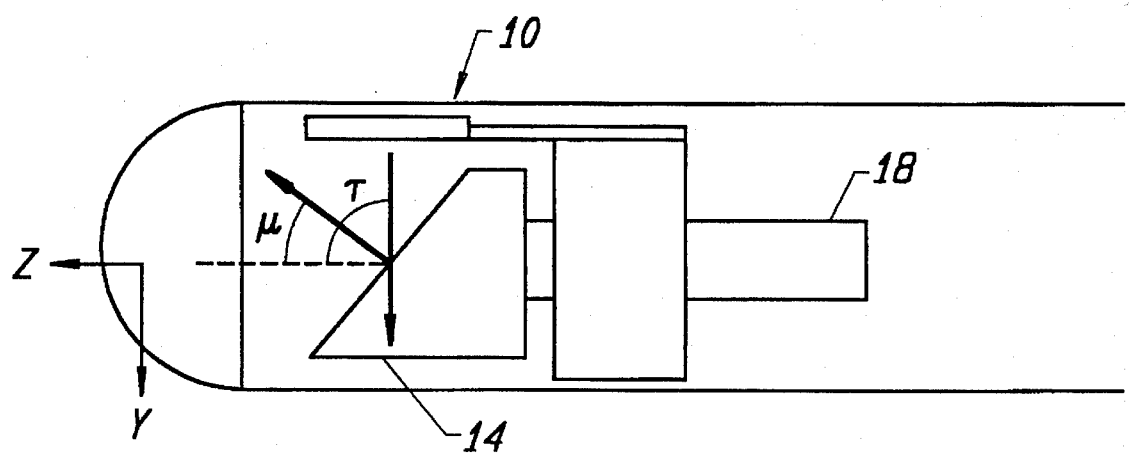
Figure 13:
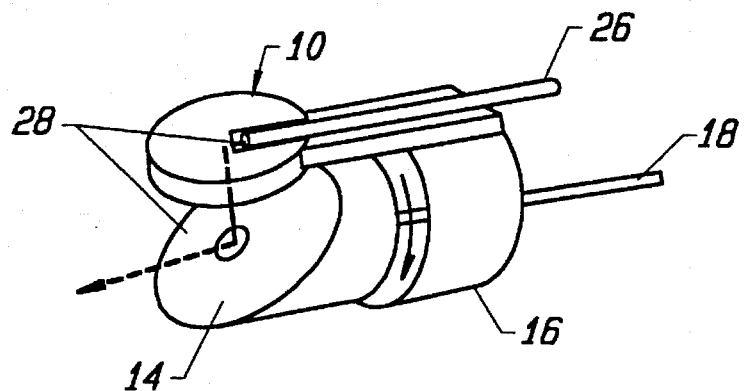
FIG. 13 is a perspective view of an imaging catheter including laser ablation.

FIGS. 1A and 1B are a perspective view and a side view of an intravascular ultrasound catheter in accordance with one embodiment of the invention in which an ultrasound transducer 10 is mounted on a bearing 12 within a catheter housing 16 with a mirror 14 rotatable in the bearing by means of drive cable 18. Transducer 10, a ceramic crystal for example, is oriented so that its normal forms an angle $\tau$ with the axis of the catheter, and the mirror, a polished stainless steel for example, is oriented so that its normal forms an angle $\mu$ with the axis of the catheter, as shown in FIG. 13. The transducer bearing and mirror are positioned in a sealed end of the catheter housing, which can be a suitable plastic tube, in a saline solution for ultrasound impedance matching with blood.

In writing the equation for the ultrasound beam direction, we define 3 unit vectors, $\vec{M}$ the normal to the ultrasound reflectors, $\vec{T}$ the normal to the ultrasound transducer and $\vec{B}$ the direction of the resultant ultrasound beam. Given $\vec{M}$ and $\vec{T}$, the direction of the ultrasound beam, $\vec{B}$, will be given by:

$$\vec{B} = \vec{T} - 2(\vec{T} \cdot \vec{M})\vec{M} \tag{1}$$

For convenience, the motion of the scanned beam can be described in a cartesian coordinate system. The long axis of the catheter will be chosen so that it lies along the z-axis. The effect of angulation of the mirror or the transducer with respect to the axis of the catheter by an angle $\alpha$ can be described by rotation of the normal vectors about the x-axis. This rotation is described mathematically by multiplication of the normal vectors by the following angulation transformation matrix, $A(\alpha)$.

$$A(\alpha) = \begin{bmatrix} 1 & 0 & 0 \\ 0 & \cos\alpha & -\sin\alpha \\ 0 & \sin\alpha & \cos\alpha \end{bmatrix} \tag{2}$$

The effect of rotation of the mirror or the transducer around the long axis of the catheter by an angle $\alpha$ is described by multiplying the normal to the mirror or the normal to the transducer, respectively, by a rotation transformation matrix, $R(\alpha)$.

$$R(\alpha) = \begin{bmatrix} \cos\alpha & -\sin\alpha & 0 \\ \sin\alpha & \cos\alpha & 0 \\ 0 & 0 & 1 \end{bmatrix} \tag{3}$$

If we choose the reference mirror and transducer orientations such that the mirror faces forward along the axis of the catheter and the transducer faces backward along the axis of the catheter, the normal to the mirror after angulating the mirror by an angle $\mu$ and rotating by an angle $\theta$ and the normal to the transducer after angulating by an angle $\tau$ and rotating by an angle $\phi$ are given by:

$$\vec{M}(\theta, \mu) = R(\theta)A(\mu)\begin{bmatrix} 0 \\ 0 \\ 1 \end{bmatrix} \tag{4}$$

$$\vec{T}(\phi, \tau) = R(\phi)A(\tau)\begin{bmatrix} 0 \\ 0 \\ -1 \end{bmatrix} \tag{5}$$

Given these formulas for the normals to the mirror and the transducer, the resulting beam direction for arbitrary angulations and rotations of the mirror and transducer can be calculated using Equation 1. The scan sectors for rotating mirror designs can be obtained by allowing the $\theta$ to vary from 0 to 360 degrees. Similarly, the scan sector for rotating transducer designs can be calculated by allowing $\phi$ to vary from 0 to 360 degrees.

The applicability of this derivation can be seen by examining the result when the mirror and transducer are in the orientations used for prior art side viewing devices. In this situation, the transducer is not angulated nor rotated, so $\tau=0$ and $\phi=0$. The mirror is angulated 45 degrees, so $\mu=45°$. $\vec{M}$, the vector normal to the mirror, is given by:

$$\vec{M}(\theta, 45°) = \begin{bmatrix} \cos\theta & -\sin\theta & 0 \\ \sin\theta & \cos\theta & 0 \\ 0 & 0 & 1 \end{bmatrix} \begin{bmatrix} 1 & 0 & 0 \\ 0 & \sqrt{2}/2 & -\sqrt{2}/2 \\ 0 & \sqrt{2}/2 & \sqrt{2}/2 \end{bmatrix} \begin{bmatrix} 0 \\ 0 \\ 1 \end{bmatrix} \tag{6}$$

Simplifying:

$$\vec{M}(\theta, 45°) = \begin{bmatrix} \frac{\sqrt{2}}{2}\sin\theta \\ -\frac{\sqrt{2}}{2}\cos\theta \\ \frac{\sqrt{2}}{2} \end{bmatrix} \tag{7}$$

and $$\vec{T}(0, 0) = \begin{bmatrix} 0 \\ 0 \\ -1 \end{bmatrix} \tag{8}$$

Inserting this into equation 1, we get:

$$\vec{B}(\theta) = \begin{bmatrix} \sin\theta \\ -\cos\theta \\ 0 \end{bmatrix} \tag{9}$$

Thus, we can see that the ultrasound beam with this configuration of transducer and mirror traverses a circle in a clockwise fashion as the mirror is rotated 360° in the clockwise direction. The scan path for a side viewing device is therefore a special case of the general solution for an ultrasound scan produced by rotating a mirror or a transducer around the catheter axis.

A forward viewing device can be seen to result from another special case. If the transducer is now angulated 90° and the mirror angulated 45°, the ultrasound beam vector will be given by:

$$\vec{B}(\theta) = \begin{bmatrix} \sin\theta\cos\theta \\ \sin^2\theta \\ \cos\theta \end{bmatrix} \quad (10)$$

This particular arrangement of mirror and transducer can be implemented as shown schematically in FIG. 1. It consists of an ultrasonic transducer mounted so that its beam is perpendicular to the long axis of the catheter and positioned so that it strikes the face of a reflecting mirror which redirects the beam in a forward direction. Both the transducer and reflecting mirror need be no different than those currently used in side viewing ultrasound catheters, although the transducer design should be thin in order to reduce the catheter profile. Methods for constructing thin transducers are known. Rotation of the mirror can be by means of a flexible drive shaft as described for most side viewing catheters but may also use other means such as miniature motors or turbines.

Figure 2:
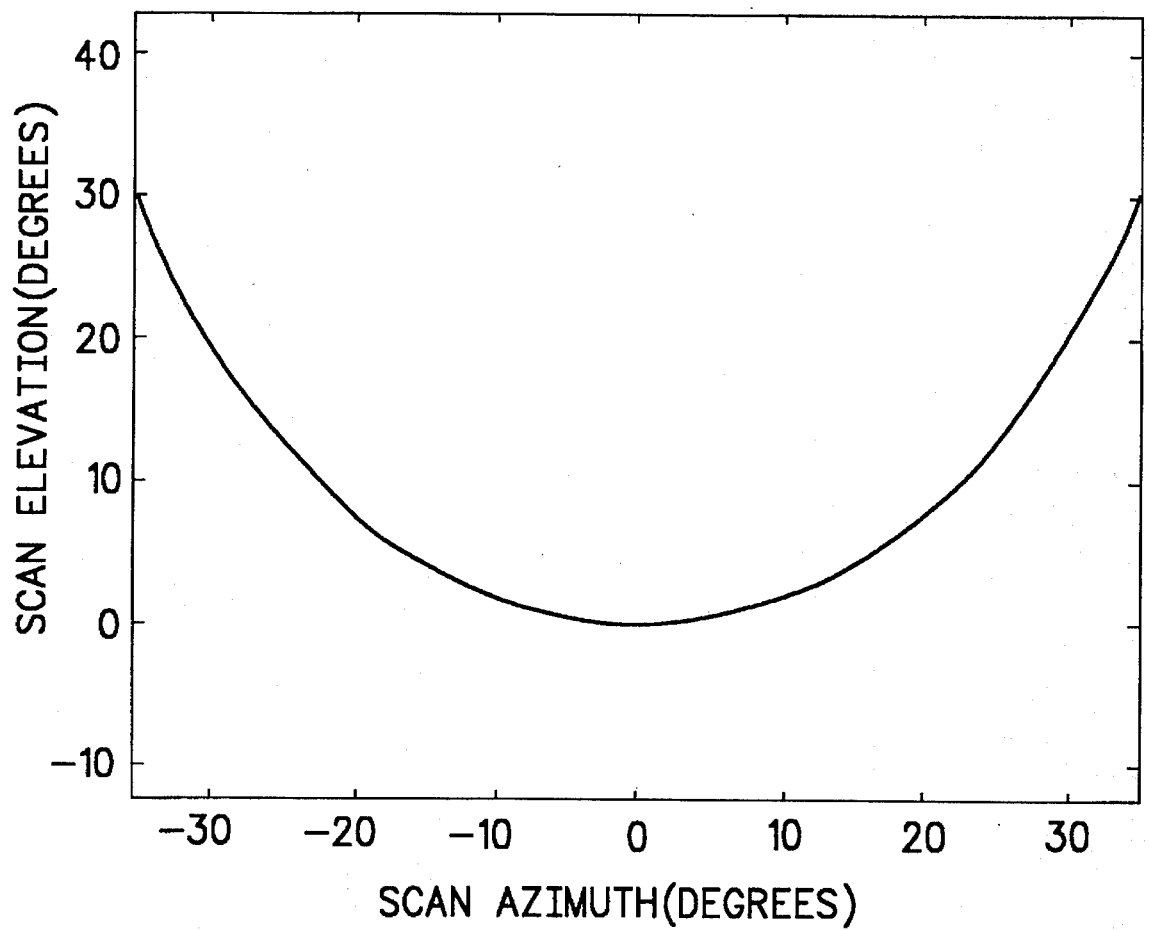
FIG. 2 illustrates scan path for the forward viewing catheter of FIG. 1.

The scan path created by such a device is shown graphically in FIG. 2. The sector scanned by this device lies approximately in the xz-plane, therefore the scan azimuth is defined to be the angle between the z-axis and the projection of the ultrasound beam onto the xz-plane. The degree to which the beam deviates from being planar is defined by the scan elevation and is the angle between the ultrasound beam and the xz-plane. The formulas for the scan azimuth and scan angle are as follows:

$$\text{scan azimuth} = \arctan(\sin\theta) \quad (11)$$

$$\text{scan elevation} = \arcsin(\sin^2\theta) \quad (12)$$

The scan sector created by this simple device is thus minimally curved for a sector extending approximately 25° to each side of midline, which gives a total sector width of 50°.

The forward viewing device described above provides a 50° viewing sector. Outside of this range, the beam path begins to deviate significantly out of plane. Slight modifications of the transducer and mirror orientation can be used to improve the flatness of the scan sector. It is still useful in these arrangements to force the ultrasound beam to point straight forward at some point during the scan. If we enforce this requirement, it can be shown that $2\mu = \tau$, where $\mu$ and $\tau$ are the angles that the normals to the mirror and to the transducer make with the long axis of the catheter. Returning to equation 1 and now substituting $2\mu$ for $\tau$, we get:

$$\vec{B} = \begin{bmatrix} \sin 2\mu(\sin 2\theta \sin^2\mu + \sin\theta\cos 2\mu) \\ \sin 2\mu(1 - 2\cos^2\theta\sin^2\mu - \cos\theta\cos 2\mu) \\ \cos\theta\sin^2 2\mu + \cos^2 2\mu \end{bmatrix} \quad (13)$$

Figure 3:
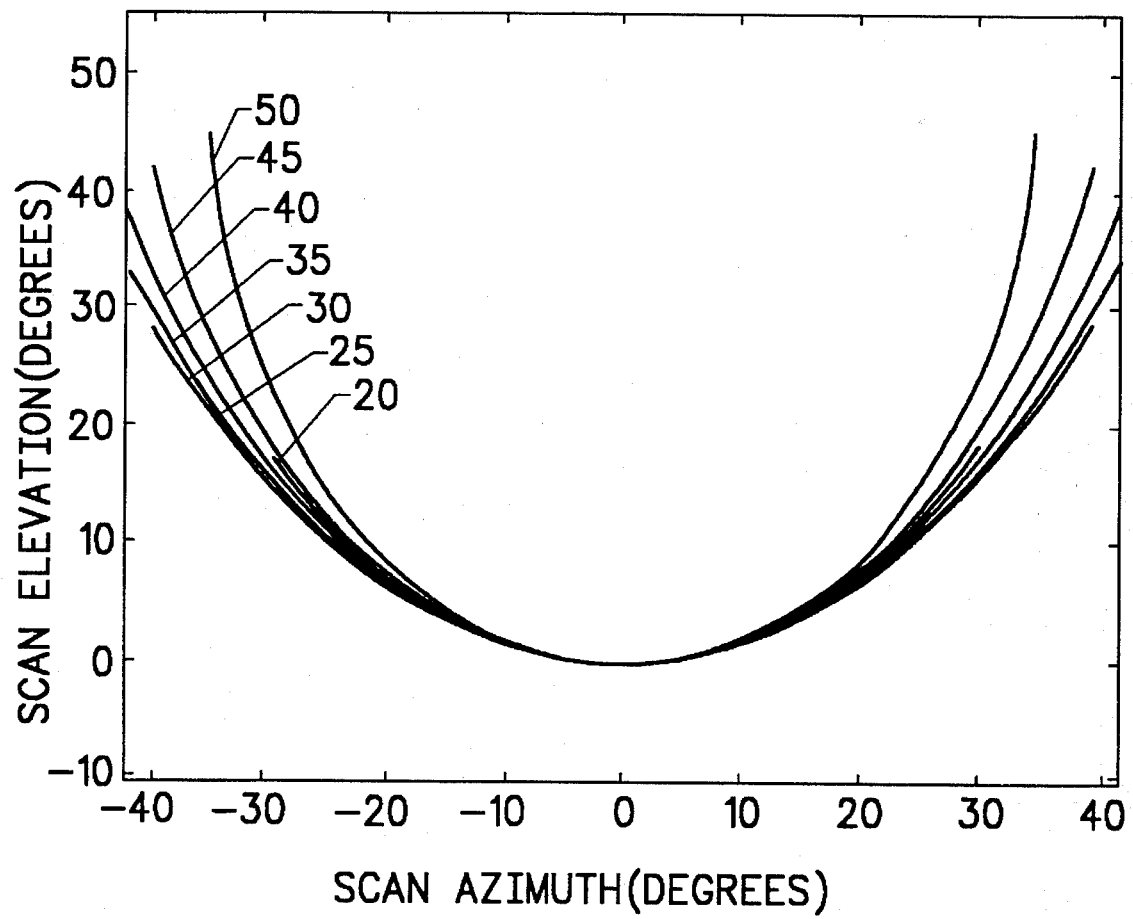
FIG. 3 illustrates scan path with a variety of mirror orientations.

The resulting scan path is then given by:

$$\text{scan angle} = \arctan(\vec{B}_x/\vec{B}_z) \quad (14)$$

$$\text{scan azimuth} = \arcsin(\vec{B}_y) \quad (15)$$

where $\vec{B}_x$, $\vec{B}_y$ and $\vec{B}_z$ are the components of the vector which is oriented along the direction of the ultrasound beam. A plot of the sectors scanned for a variety of mirror orientations is shown in FIG. 3. Each line represents a change of 5° in the orientation of the mirror. The flattest scan sector results from a mirror angle of ~30° and a transducer angle of ~60°. A gain of 5° in sector size is achieved by using an oblique mirror and transducer angle when compared to the simple design presented in the previous section when using 10° as the limit to which the beam can deviate from a planar scan. This improvement may not be clinically important.

Figure 4:
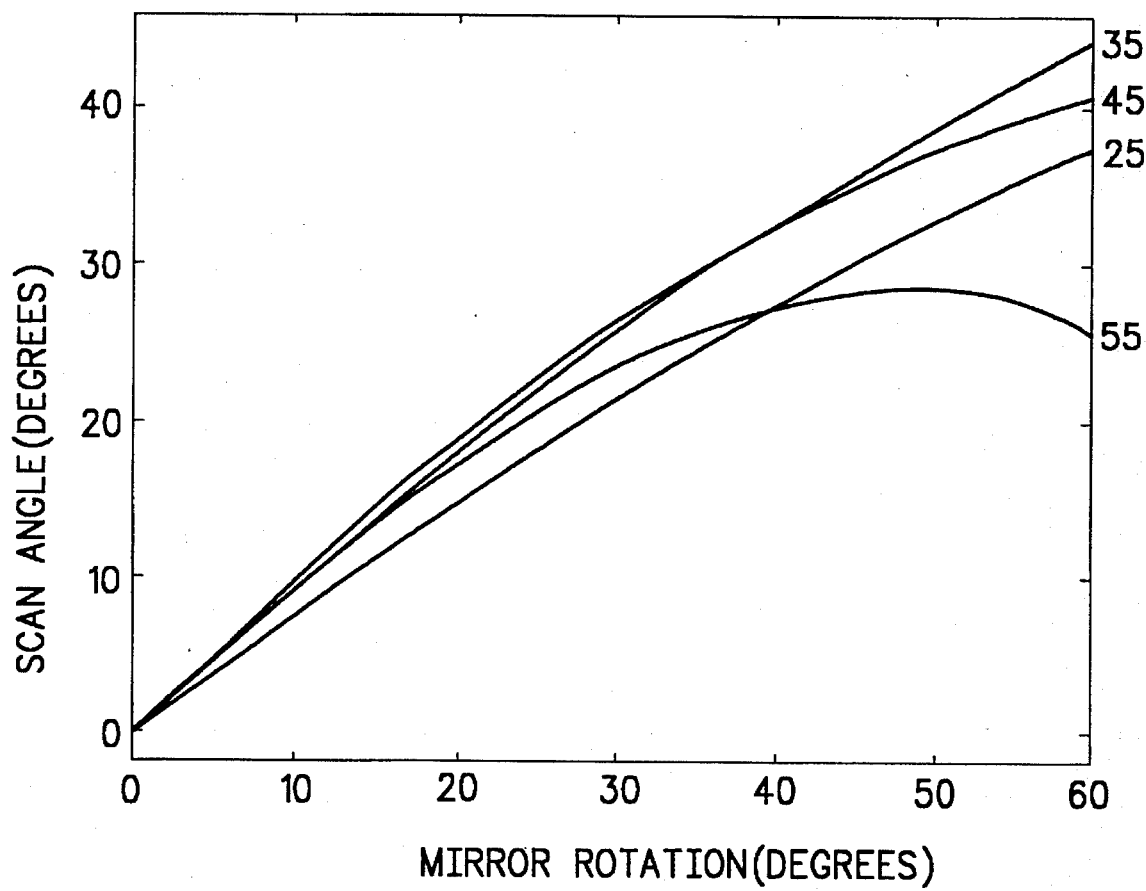
FIG. 4 illustrates scan angle resulting from mirror rotation for a variety of mirror orientations.

Since the scan azimuth is not equal to the angle of rotation of the mirror, a correction will be needed prior to scan conversion to avoid distortion. The correction is given in FIG. 4 for a variety of mirror orientations.

An additional issue that must be addressed is the reduction in imaging aperture as the mirror is rotated. As the mirror is rotated, the ultrasound beam becomes progressively more oblique to the mirror which will result in loss of power received and transmitted, as well as some loss in resolution due to increased diffraction effects. If we assume that the entire wave reflected off the mirror strikes the transducer during receiving and conversely that the entire surface of the mirror is insonified by the transducer during transmission, then the effective aperture of the device is given by $(\vec{B} \cdot \vec{T}) \times$ mirror area. Referring back to equation 13, we get:

$$\text{Aperture area} = (\cos\theta\sin\mu\sin 2\mu + \cos\mu\cos 2\mu) \times \text{mirror area} \quad (16)$$

The change in aperture with mirror rotation is actually more relevant and can be obtained by dividing by the maximum aperture. The maximum aperture occurs when $\theta = 0$, therefore the maximum aperture achieved is $\cos\mu \times$ mirror area. The relative aperture size is then given by:

$$\text{Relative aperture area} = 2\cos\theta\sin^2\mu + \cos 2\mu \quad (17)$$

Figure 5:
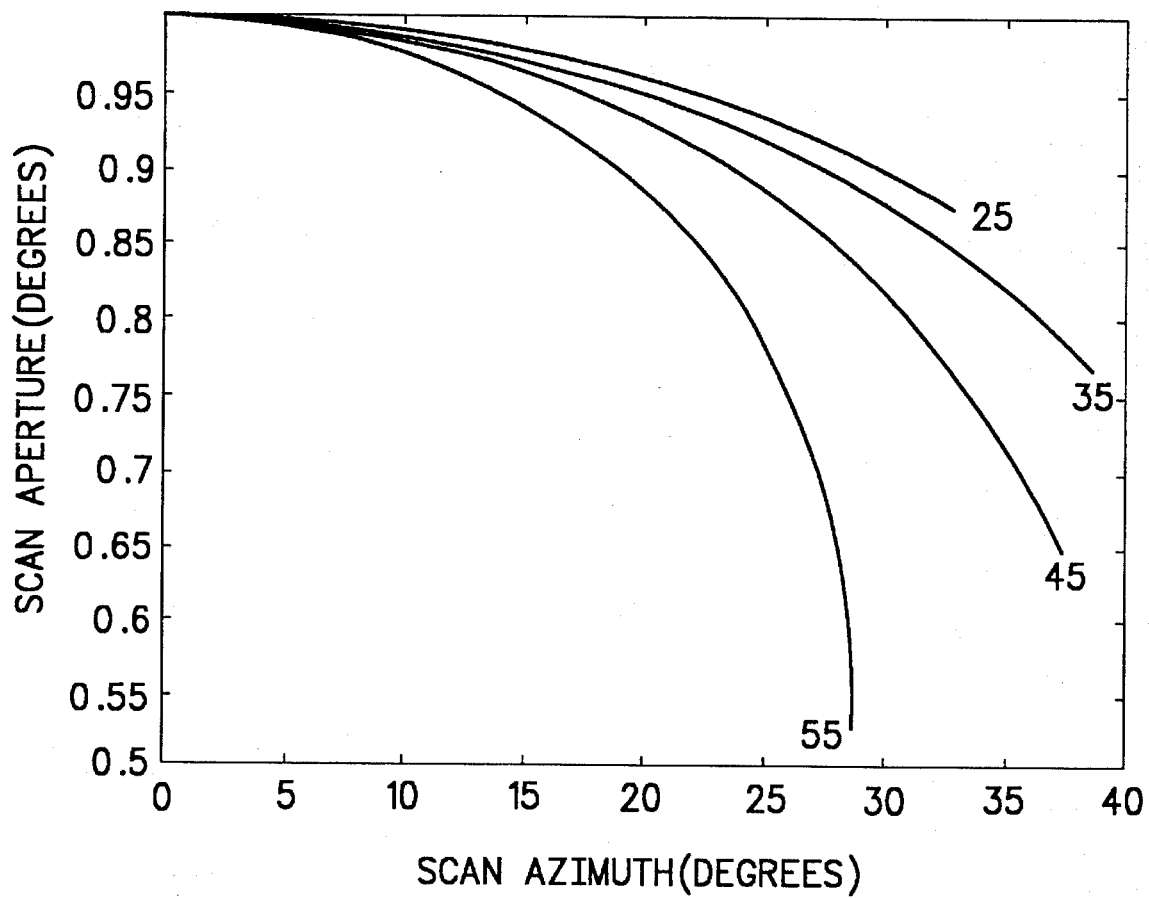
FIG. 5 illustrates relative aperture as a function of ultrasound beam angle for various mirror orientations.

The resulting relative aperture as a function of the beam angle is shown in FIG. 5. It is apparent that some improvement in image aperture is achieved with a mirror pointed more coaxially with the catheter. The gain is not large and by the point in the scan at which the aperture begins to be compromised significantly, the scan will have already deviated from the scan plane considerably. Within the useful scan sector, the loss in aperture is only 10% and should not be significant.

Figure 6A:
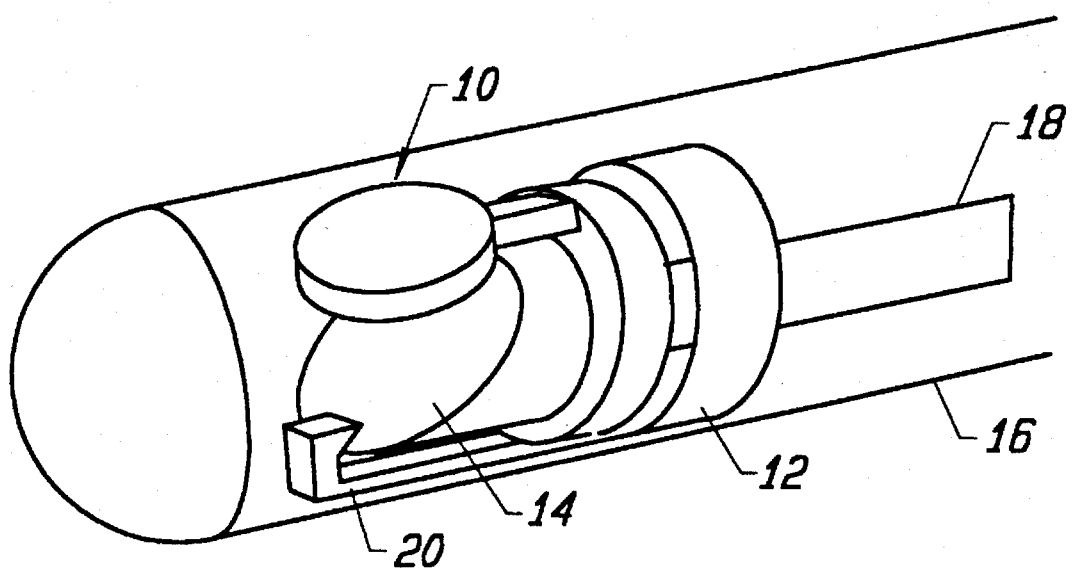
FIGS. 6A, 6B are a perspective view and a section view of a catheter in accordance with another embodiment of the invention.
Figure 6B:
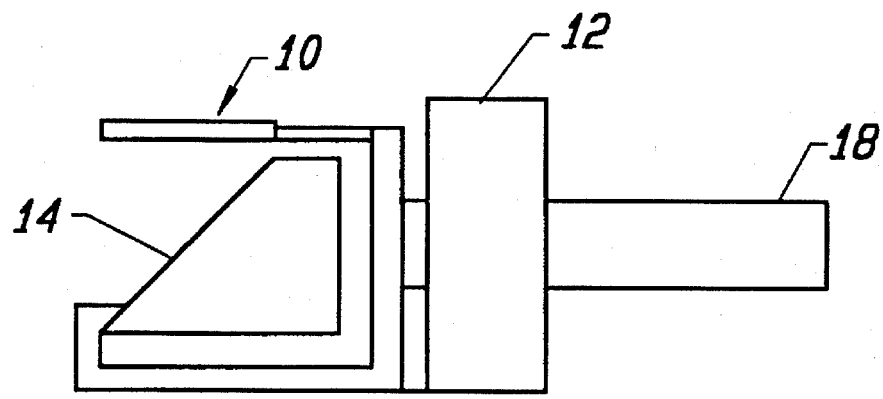

Consider now the goal of achieving a planar scan sector. The forward viewing devices described above do not achieve this ideal scan sector but produce a reasonable approximation for moderate sized scan sectors. The non-planar nature of the scan sector can be addressed by adopting a moving transducer design. A diagram illustrating one embodiment of a moving transducer device is shown in FIG. 6. Like elements in FIGS. 1 and 6 have the same reference numerals. Strut 20 rigidly mounts mirror 14 to bearing 12, and transducer 10 is free to rotate within bearing 12. If the transducer and mirror are oriented as they are for a rotating mirror design and we continue to keep the constraint that the beam is coaxial with the catheter at some point during the scan, we get for the beam direction:

$$\vec{B} = \begin{bmatrix} -\sin\phi\sin 2\mu \\ \sin 2\mu\cos 2\mu(\cos\phi - 1) \\ \cos\phi\sin^2 2\mu + \cos^2 2\mu \end{bmatrix} \quad (18)$$

The resulting scan angle and scan can be determined from the components of $\vec{B}$ as before.

Of note when $\mu = 45°$ then $$\vec{B} = \begin{bmatrix} -\sin\phi \\ 0 \\ \cos\phi \end{bmatrix} \quad (19)$$

Figure 7:
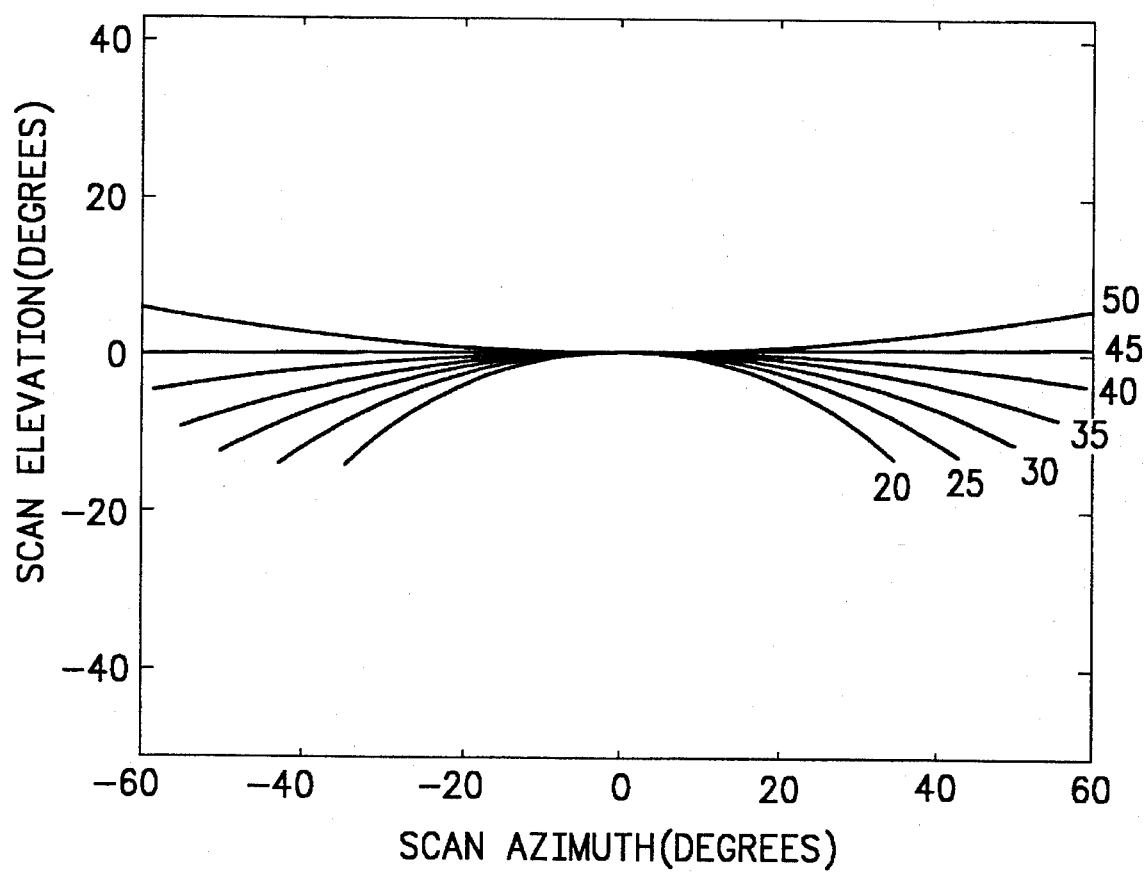
FIG. 7 illustrates scan sectors for the embodiment of FIG. 6.

It is easy to see that the ultrasound beam in a device of this design produces a beam that stays in the xz-plane and is oriented at angle −ϕ away from the axis of the catheter when the transducer has been rotated by angle ϕ. This would be the ideal scan sector with linear correspondence between mirror rotation and beam angle and a large planar scan sector. The scan sectors resulting from other mirror and transducer orientations are shown in FIG. 7. In general for all mirror orientations the scan sector remains much more planar with a moving transducer design than with a moving mirror design.

Figure 8:
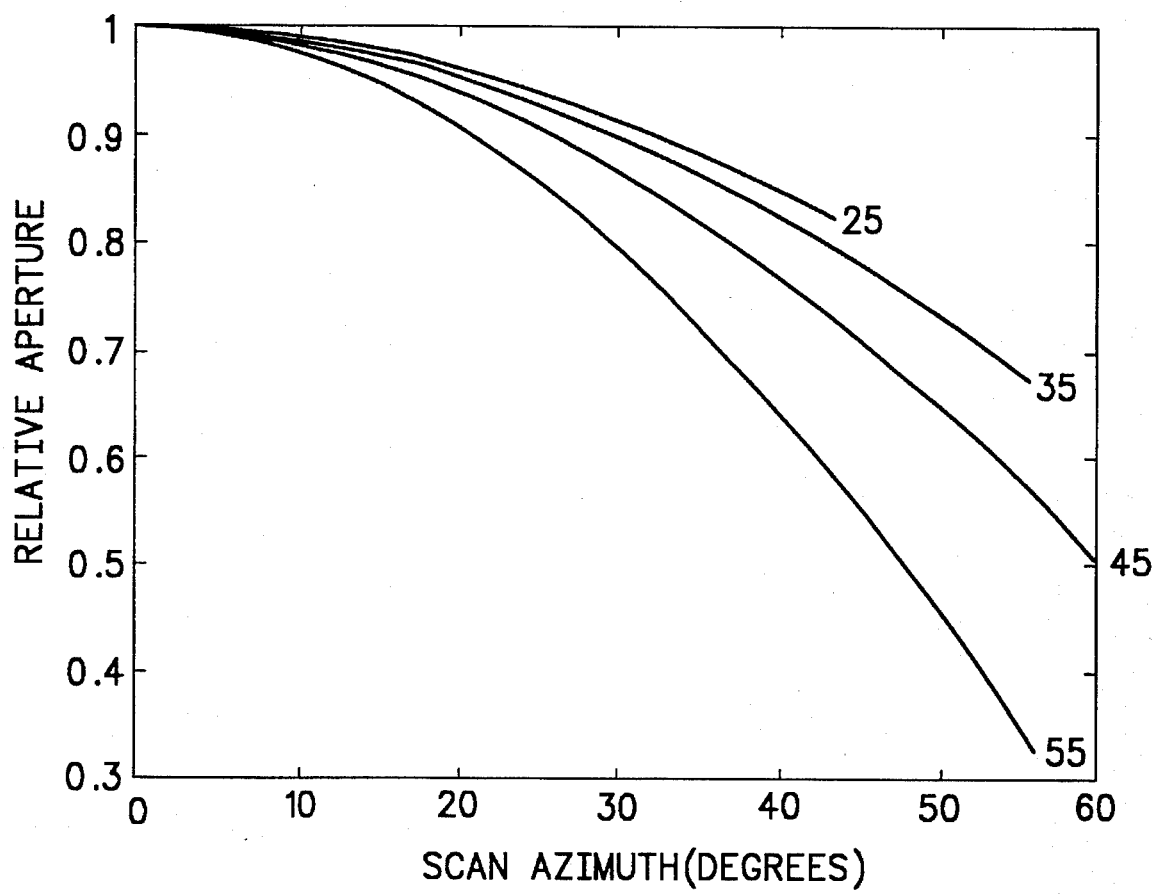
FIG. 8 illustrate relative imaging aperture as a function of scan angle.

The device will suffer from decreased aperture size as the beam becomes more oblique to the surface of the mirror. It is easily shown that the device aperture is only dependent on the difference between the angle of rotation of the mirror and transducer, thus we may use the result from equation 17. The relative aperture as a function of scan azimuth is shown in FIG. 8. In contrast with the rotating mirror design which had a scan sector limited by deviation of the beam out of the scan plane, we see that for mirror orientations near 45°, the limiting constraint on the scan sector size is the loss of aperture when the beam is scanned to the side. For scan sectors less than 90° the loss in aperture is less than 30% and should be acceptable. A slightly shallower mirror angle can improve the imaging aperture to some degree, the improvement, however, is slight for sector sizes up to 90° in width.

For a rotating transducer design and to a lesser degree for rotating mirror designs, the overall catheter diameter will be significantly affected by the width of the transducer. For planar mirrors and transducers, both the mirror and transducer must be of the same dimension to achieve maximal aperture, thus the effective aperture of both the rotating mirror and the rotating transducer designs device will not be able to reach the theoretical maximum for a given catheter size, since a significant amount of space is needed to house the transducer. In particular, the moving transducer design requires more space to provide clearance for the transducer as it rotates around the mirror. If a focusing mirror is used, the transducer may be made smaller without any change in the imaging aperture of the device and thus would permit a decrease in catheter diameter. Additionally, a smaller transducer is advantageous for those designs where the transducer is oriented at less than 90° since in those designs the transducer will impede part of the beam reflected from the mirror unless it is set back from the mirror.

Figure 9:
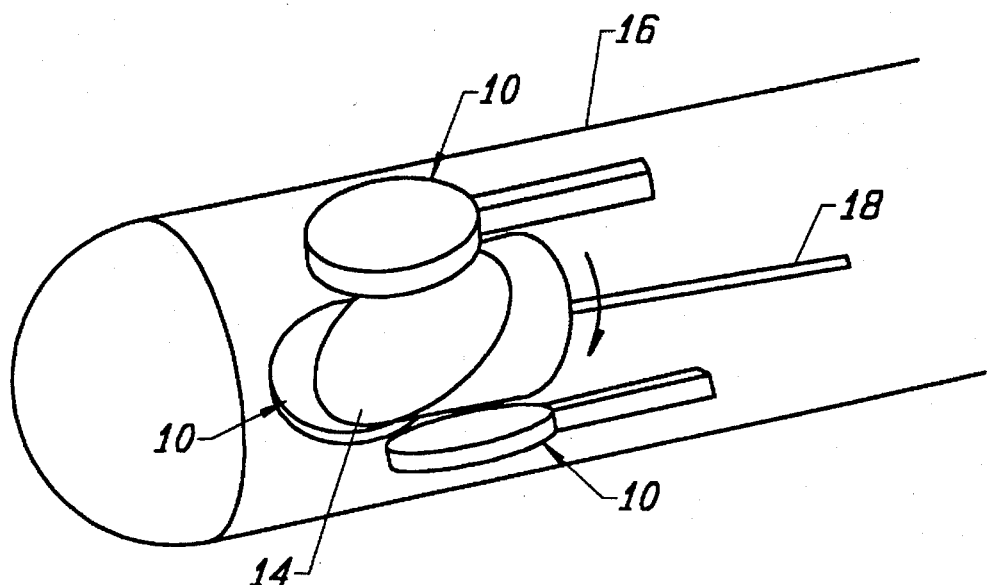
FIG. 9 is a perspective view of a multi-transducer imaging catheter in accordance with another embodiment of the invention.

The scan of the sector is achieved in less than 120° of rotation of the mirror for most choices of mirror and transducer angles. Therefore, most of the duration of any rotation of the mirror will be spend in positions which are not useful for creating scan data. This scan time can be recovered by the addition of more transducers. For example, the use of three transducers 10 spaced equally around the catheter 16, as shown in FIG. 9, adds two additional scan sectors, each rotated 60° from the other. This approach may be applied to both a moving mirror or a moving transducer design.

Three dimensional imaging is feasible for intravascular ultrasound at acceptable frame rates because of the relatively shallow depth of penetration needed. For a depth of penetration of 1.0 cm at a scan rate of 15 frames per second, a total of 5,000 A-lines may be obtained. This will allow the forward field of view to be scanned by a 70 by 70 grid of A-lines. The resulting scan line spacing closely approximates the beam width for achievable imaging apertures.

The multiscan approach can be extended to many transducers, thus creating a multiplicity of sector planes. If enough planes are scanned, a three-dimensional image is produced. The number of wires required for such an approach may limit its suitability for generating C-scan (three-dimensional) imaging, although multiplexing schemes may be implemented to reduce the number of wires required.

Figure 10A:
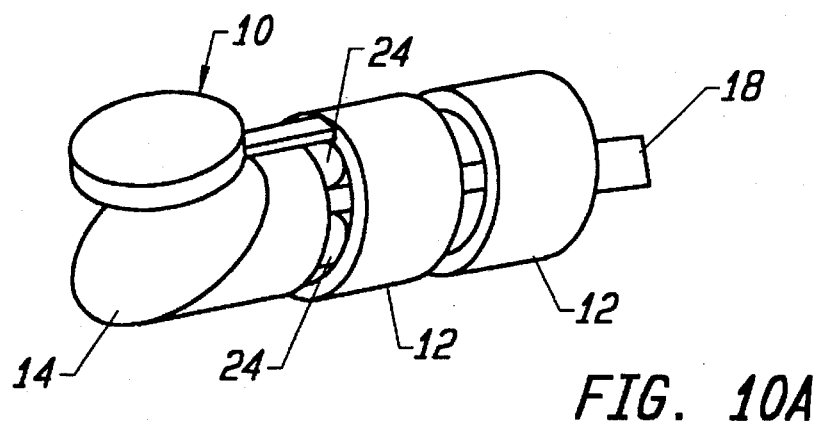
FIGS. 10A, 10B are a perspective view and an end view of an imaging catheter including planetary gears for generating coordinated mirror and transducer motion.
Figure 10B:
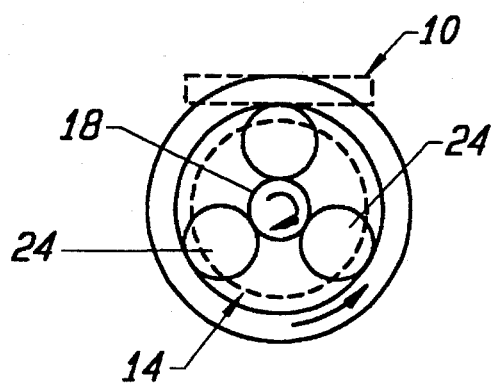

An alternative approach is to move the transducer after each sector is obtained. The transducer position may be rotated around the axis of the catheter or displaced along the axis of the catheter. Rotation of the transducer results in a series of sector scans which are gradually rotated around the axis of the catheter. Displacement of the transducer results in each scan sector being displaced in azimuth from the previous. Either approach results in a three-dimensional scan. Both these approaches have the disadvantage of requiring the coordinated motion of both the mirror and the transducer. One approach to generating the coordinated motion of the mirror and transducer is to drive the transducer motion via a set of planetary gears 24, as shown in FIG. 10. The diameters of the gears are chosen to achieve the desired ratio of transducer rotation to mirror rotation. Each rotation of the mirror will then start with the transducer in a slightly different orientation and thus the sectors scanned by the mirror motion will offset in angle from each other.

A B-scan or C-scan requires the controlled deviation of the ultrasound beam away from the catheter axis. A prior art device uses a system of mechanical cams to convert rotary motion into the proper angulation of a transducer. In accordance with the invention, the angulation is achieved by reflecting the ultrasound beam off a rotating mirror.

The forward viewing catheters described above use a mirror moving relative to a transducer to achieve a forward viewing scan. An alternative approach is to tilt the transducer and thus directly redirect the ultrasound beam. This approach has been previously proposed using a system of cams and follower pins to convert the rotary motion provided by the drive cable in to the necessary tilting motion. This mechanical approach however limits the size of the catheter because of its mechanical complexity.

A more direct approach is to use microactuators located at the tip of the catheter to directly generate the motion needed. The microactuators can be electrostatic, electromagnetic, or unimorphs or monomorphs based on thermal or piezoelectric effects.

Figure 11:
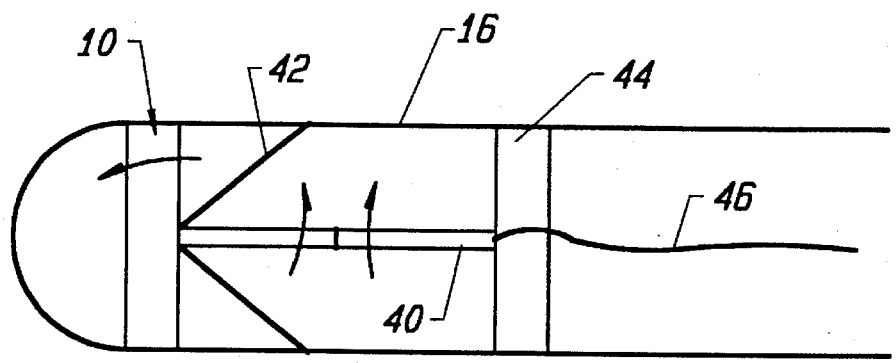
FIGS. 11, 12 are side views of imaging catheters which employ rotatable ultrasound transducers in accordance with embodiments of the invention.

One embodiment is shown in side-view in FIG. 11. In this embodiment the transducer 10 is mounted on a shaft 40, including a unimorph or monomorph actuator in cylindrical housing 16. The shaft is then passed through a hole in the tip of a hollow stainless steel cone 42, positioned in housing 16, and is supported at an opposing end by support disk 44. Wires 46 energize the unimorph or monomorph. The end of the shaft is then deviated from side to side with the unimorph or monomorph actuator. The cone acts as a fulcrum thus resulting in tilting of the transducer from side to side. The use of two actuators mounted 90 degrees from each other would give the potential to scan in two directions and thus provide 3-dimensional imaging.

Figure 12:
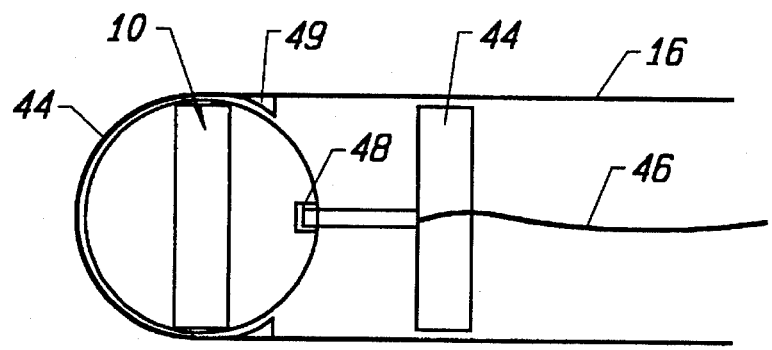

An alternative design is shown in FIG. 12. Here the transducer 10 is mounted in a echolucent hemisphere or sphere 44 with a rubber or absorbent material as a backing for the transducer. Such echolucent material is well-known, such as ATV-66. The sphere is free to rotate in a socket 49 at the tip of the catheter. A small hole 48 is placed in the back of the sphere into which the tip of a microactuator 40 is inserted. As the tip of the microactuator is deviated from side to side under electronic control the sphere will be rotated, thus tilting the transducer.

The imaging probe can be combined with a laser to allow ablation of atheroma while under the guidance of simultaneous intravascular ultrasound. One method for achieving this is to carry the laser energy to the catheter tip in optical fibers as shown in FIG. 13. At the catheter tip, the light energy is allowed to leave the fiber 26 and is redirected by mirror 28 so that its path is coaxial with the beam generated by the ultrasound transducer. This polished stainless steel mirror is reflective to ultrasound waves and laser waves. The laser beam and the ultrasound beam are then scanned in unison by the rotating mirror. This necessitates that the ultrasound mirror also function as an optical mirror. By switching the laser on and off in correspondence with the mirror rotation, a particular point in the atheroma as identified by ultrasound may be selectively ablated.

To demonstrate the principle of this device, a 10 Fr and a 4.3 Fr commercial side viewing intravascular ultrasound catheter were modified to achieve the geometry shown in FIG. 1. The mirror angle was 45° and transducer was oriented perpendicular to the catheter. This design was used because of the simplicity of manufacture.

Both probes were driven with a commercial intravascular ultrasound machine (CVIS Insight). A pulse frequency of 10 MHz was used with the 10 Fr probe and 30 MHz was used with the 4.3 Fr probe.

Figure 14:
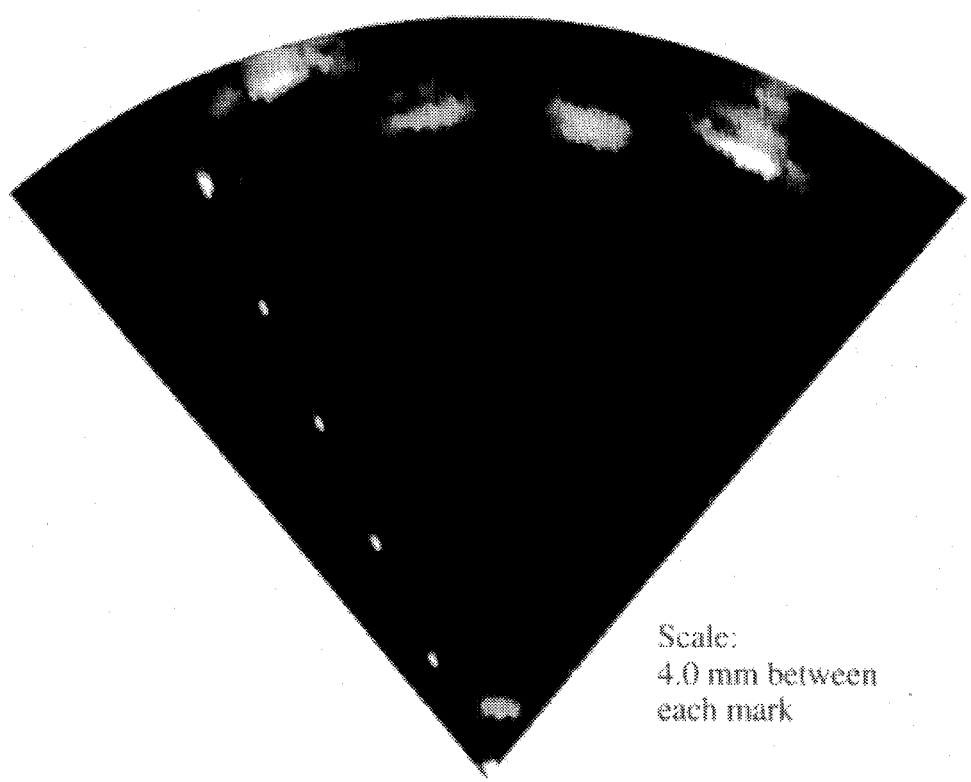
FIGS. 14–17 are images generated with an intravascular ultrasound imaging catheter in accordance with the invention.
Figure 15:
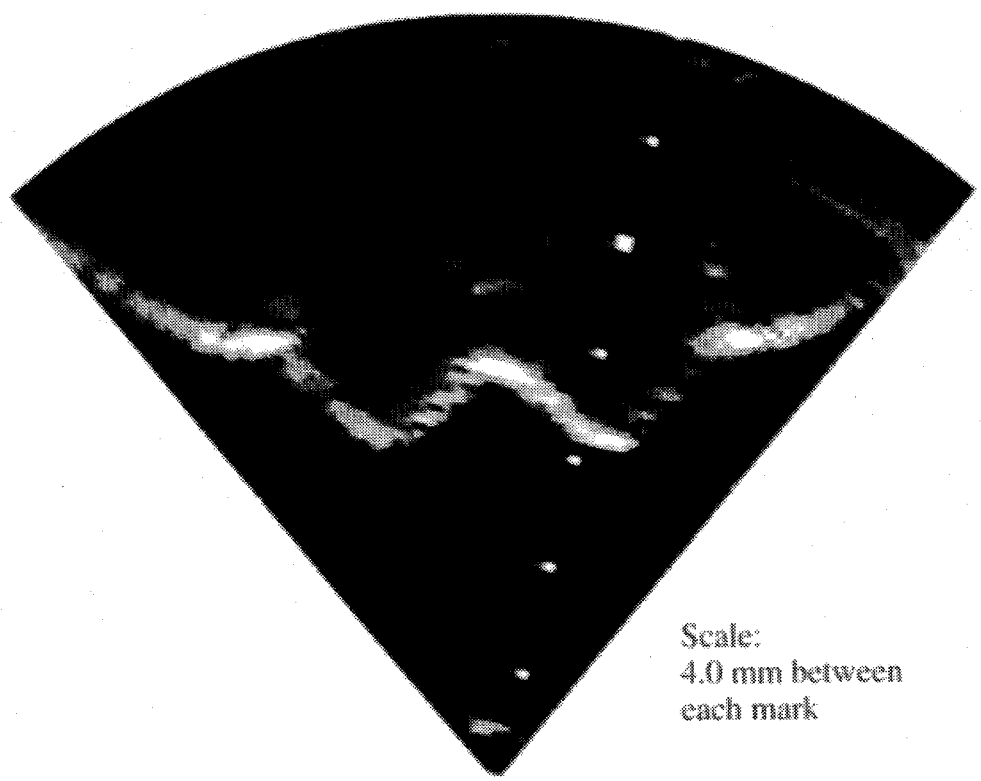

The images shown in FIGS. 14 and 15 were obtained with the 10 Fr probe. No correction for the less than one to one correspondence between the mirror rotation and the scan angle was performed, therefore there is some distortion at the edges of the images. The actual images have been cropped to remove the portion of the scan time in which no useful information is obtained.

Figure 16:
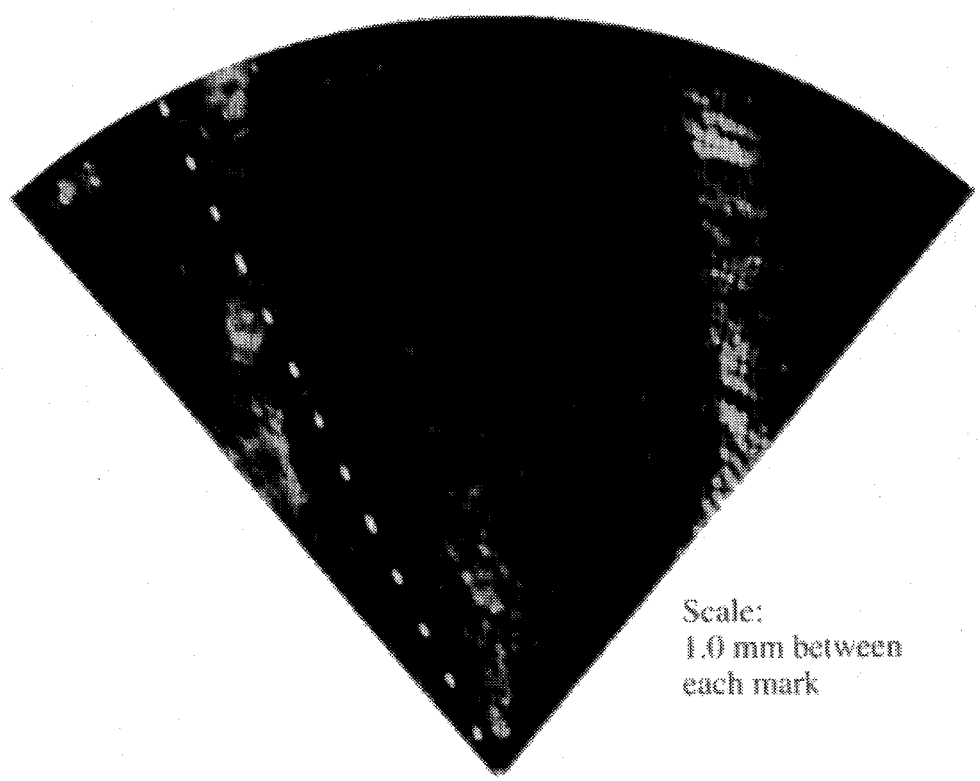
Figure 17:
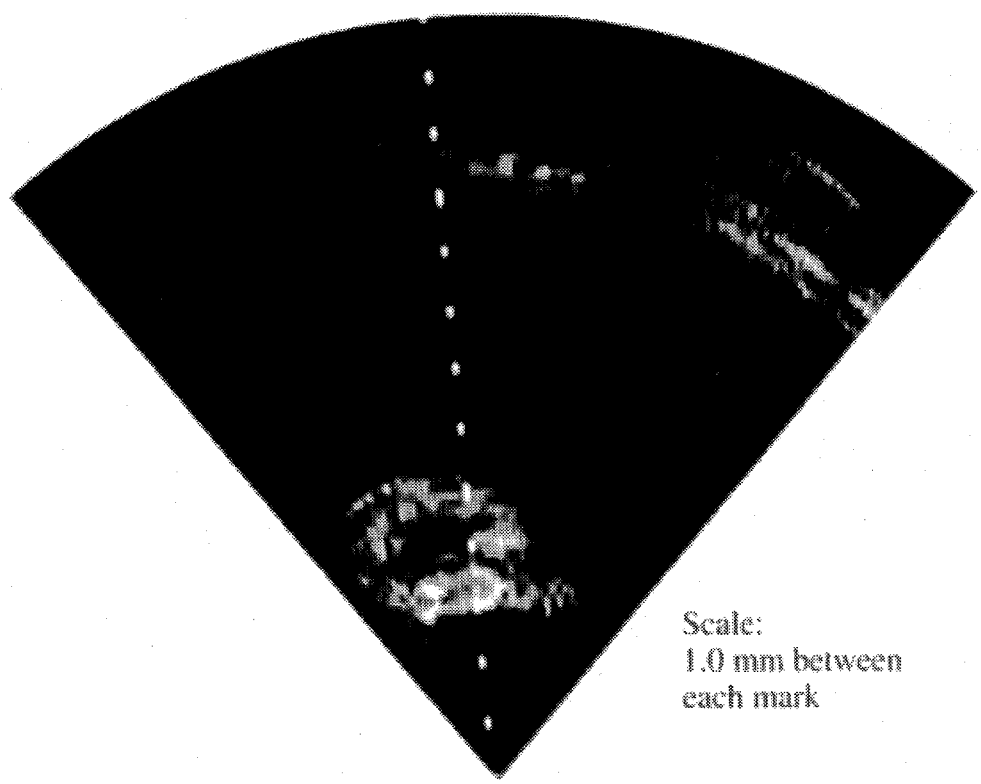

Imaging has also been performed upon cadaver tissue. FIG. 16 was obtained with a 4.3 Fr catheter operating at 30 MHz. The catheter was placed in the lumen of a freshly explanted human cadaver aorta. This vessel was without disease as is evidenced by the smooth vessel walls on the ultrasound image. A cross section of a small vessel arising from the aorta is shown in FIG. 17. The lumen of the small vessel is quite easily identified.

A design for a simple and compact forward viewing catheter has been described. Design considerations for optimal scan trajectory and aperture are reviewed, and improving the scan rate using multiple transducers is described. Implementing two-dimensional scanning to collect real time three-dimensional datasets is also described.

While the invention has been described with reference to specific embodiments, the description is illustrative of the invention and is not to be construed as limiting the invention. Various modifications and applications might occur to those skilled in the art without departing from the true spirit and scope of the invention as defined by the appended claims.

What is claimed is:

1. An ultrasound imaging catheter comprising a catheter having a first end extending along a longitudinal axis, bearing structure mounted near said first end for supporting a transducer and mirror, said bearing structure permitting rotation about an axis extending in a generally forward direction relative to said first end, an ultrasound transducer and an ultrasound mirror supported by said bearing structure to direct ultrasound waves in said generally forward direction relative to said first end, said transducer being offset from said longitudinal axis, and drive means for imparting relative rotational motion to said transducer and said mirror whereby an ultrasound beam is translated generally in a pattern extending in said forward direction.

2. The catheter as defined by claim 1 wherein said mirror is stationarily attached to said bearing structure and said transducer is rotated in said bearing by said drive means.

3. The catheter was defined by claim 1 wherein said transducer is stationarily attached to said bearing structure and said mirror is rotated in said bearing means.

4. The catheter as defined by claim 3 and further including at least a second ultrasound transducer stationarily attached to said bearing structure.

5. The catheter as defined by claim 4 wherein three ultrasound transducers are stationarily attached to said bearing structure, said transducers being spaced around said mirror by approximately 120 degrees.

6. The catheter as defined by claim 5 wherein the transducers are selectively energized.

7. The catheter as defined by claim 4 wherein the transducers are selectively energized.

8. The catheter as defined by claim 1 wherein said bearing structure includes planetary gears to impart motion to said transducer and to said mirror.

9. The catheter as defined by claim 1 wherein said drive means includes interconnect means for transferring electrical signals to said transducer for generating ultrasonic waves and for receiving electrical signals from said transducer in response to reflected ultrasonic waves.

10. The catheter as defined by claim 1 wherein said transducer comprises a ceramic crystal and said mirror comprises stainless steel.

11. The catheter as defined by claim 1 further including an optical transmission means for transmitting a laser beam for ablation of atheroma while under the guidance of simultaneous intravascular ultrasound.

12. The catheter as defined by claim 11 wherein said optical transmission means comprises an optical fiber for directing said laser beam to said mirror, said mirror being reflective to said laser beam and to ultrasound.

13. The catheter as defined by claim 1 wherein said ultrasound beam is translated in a plurality of patterns extending in said forward direction to provide three dimensional imaging.

14. An ultrasound imaging catheter comprising a catheter having a distal end and a longitudinal axis, ultrasound means mounted within said catheter and spaced from said longitudinal axis for generating an ultrasound beam at an angle to said longitudinal axis, a mirror mounted within said catheter adjacent to the distal end for redirecting said ultrasound beam in a forward direction, and means for imparting relative rotational motion between said ultrasound means and said mirror whereby said ultrasound beam is redirected generally in a pattern extending forward of said distal end, said relative rotational motion being about an axis extending in a generally forward direction.

15. An ultrasound imaging catheter as in claim 14 wherein the angle between the longitudinal axis of the catheter and the normal to the mirror is one half of the angle between the longitudinal axis of the catheter and the normal to the transducer.

16. An ultrasound imaging catheter as in claim 14 wherein the ultrasound means is an ultrasound transducer.

17. An ultrasound imaging catheter as in claim 14 wherein the ultrasound means is formed by multiple transducers arranged around the mirror.

18. An ultrasound imaging catheter as in claim 17 wherein the shifting of the direction of the ultrasound beam is accomplished by selectively energizing said transducers.

19. An ultrasound imaging catheter as in claim 14 wherein the means for imparting relative rotational motion is a flexible drive shaft.

20. An ultrasound imaging catheter as in claim 14 wherein differential rotational motion of both the mirror and transducer means is accomplished through the use of a planetary gear system.

21. An ultrasound imaging catheter as defined in claim 14 further including an optical transmission means for transmitting a laser beam for ablation of atheroma while under the simultaneous guidance of intravascular ultrasound.

22. An ultrasound imaging catheter as defined in claim 21 wherein the optical transmission means includes an optical fiber for transmitting the laser energy along the length of the catheter.

23. An ultrasound imaging catheter as defined in claim 21 wherein the optical transmission means includes a combined ultrasound and optical mirror to redirect the laser energy in the same direction as the ultrasound beam.

24. The catheter as defined by claim 14 wherein said ultrasound beam is translated in a plurality of patterns extending in said forward direction to provide three dimensional imaging.

* * * * *